US009254082B2

(12) United States Patent
Wada et al.

(10) Patent No.: US 9,254,082 B2
(45) Date of Patent: Feb. 9, 2016

(54) METHOD OF MEASURING THE ELASTICITY OF CRYSTALLINE LENS, A METHOD OF DETERMINING WHETHER CRYSTALLINE LENS IS PRESBYOPIC, AN APPARATUS FOR MEASURING THE ELASTICITY OF CRYSTALLINE LENS AND AN APPARATUS FOR DETERMINING WHETHER CRYSTALLINE LENS IS PRESBYOPIC

(71) Applicant: RIKEN, Saitama (JP)

(72) Inventors: Satoshi Wada, Saitama (JP); Kazuo Tsubota, Tokyo (JP); Atsushi Shinjo, Kanagawa (JP)

(73) Assignee: RIKEN, Saitama (JP)

( * ) Notice: Subject to any disclaimer, the term of this patent is extended or adjusted under 35 U.S.C. 154(b) by 0 days.

(21) Appl. No.: 14/203,595

(22) Filed: Mar. 11, 2014

(65) Prior Publication Data

US 2015/0022781 A1 Jan. 22, 2015

(30) Foreign Application Priority Data

Jul. 16, 2013 (JP) ................. 2013-147897

(51) Int. Cl.
*A61B 3/10* (2006.01)
*A61B 3/117* (2006.01)
(52) U.S. Cl.
CPC ................. *A61B 3/1173* (2013.01)
(58) Field of Classification Search
USPC .................. 351/200–246
See application file for complete search history.

(56) References Cited

U.S. PATENT DOCUMENTS

| 8,262,646 | B2 * | 9/2012 | Frey et al. | 606/4 |
| 8,801,186 | B2 * | 8/2014 | Frey et al. | 351/221 |
| 2009/0177189 | A1 * | 7/2009 | Raksi | 606/4 |
| 2013/0237969 | A1 * | 9/2013 | Hohla et al. | 606/4 |
| 2014/0135752 | A1 * | 5/2014 | Duma et al. | 606/6 |

FOREIGN PATENT DOCUMENTS

| JP | S58-206718 A | 12/1983 |
| JP | H06-217939 A | 8/1994 |

OTHER PUBLICATIONS

Heys et al., "The stiffness of human cataract lenses is a function of both age and the type of cataract," research paper, Jan. 3, 2008, pp. 701-703, Experimental Eye Research 86 (2008), Elsevier Ltd., available online.

Burd et al., "An improved spinning lens test to determine the stiffness of the human lens", research paper, Oct. 30, 2010, pp. 28-39, Experimental Eye Research 92 (2011), Elsevier Ltd., available online.

Sharma et al., "A comparative study on the viscoelastic properties of human and animal lenses," research paper, Sep. 5, 2011, pp. 681-688, Experimental Eye Research 93 (2011), Elsevier Ltd., available online.

(Continued)

*Primary Examiner* — Mohammed Hasan

(57) ABSTRACT

The present invention provides a method of measuring the elasticity of crystalline lens and an apparatus for measuring the elasticity of the crystalline lens for measuring stiffness of the crystalline lens 1, wherein the crystalline lens 1 is irradiated with pulse laser light to generate photoelastic waves from the crystalline lens 1, and the photoelastic waves from the crystalline lens 1 are measured.

5 Claims, 6 Drawing Sheets

(56) References Cited

OTHER PUBLICATIONS

Bailey et al., "Light-Scattering Study of the Normal Human Eye Lens: Elastic Properties and Age Dependence," research paper, Dec. 2010, pp. 2910-2917, IEEE Transactions on Biomedical Engineering, vol. 57, No. 12.

Schachar et al., "Viscoelastic properties of fresh human lenses under 40 years of age: implications for the aetiology of presbyopia," journal, Mar. 28, 2011, pp. 1010-1013, British Journal of Ophthalmology, vol. 95 issue 7, published online first.

* cited by examiner

Fig. 3
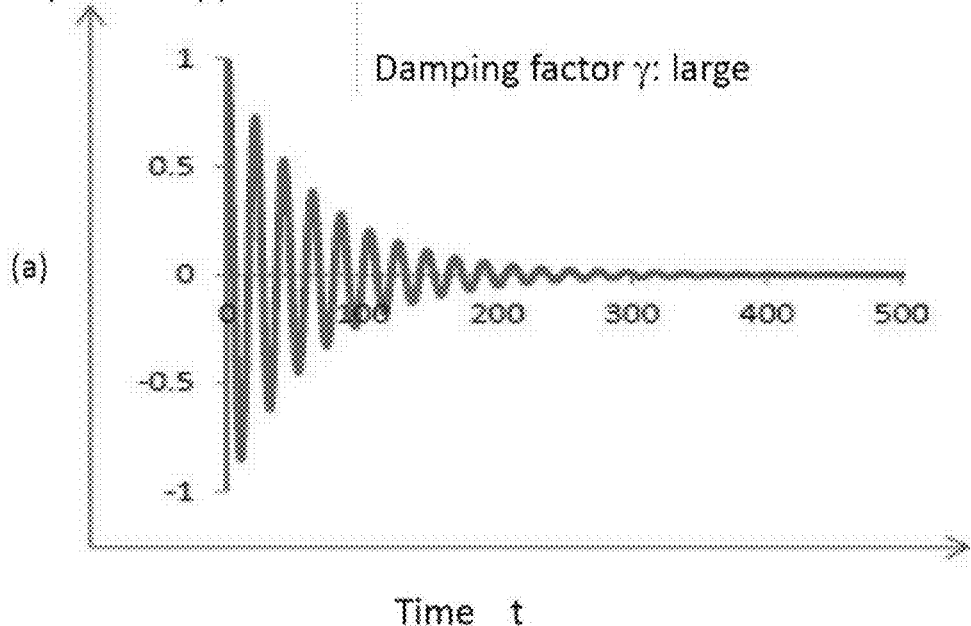
(a)
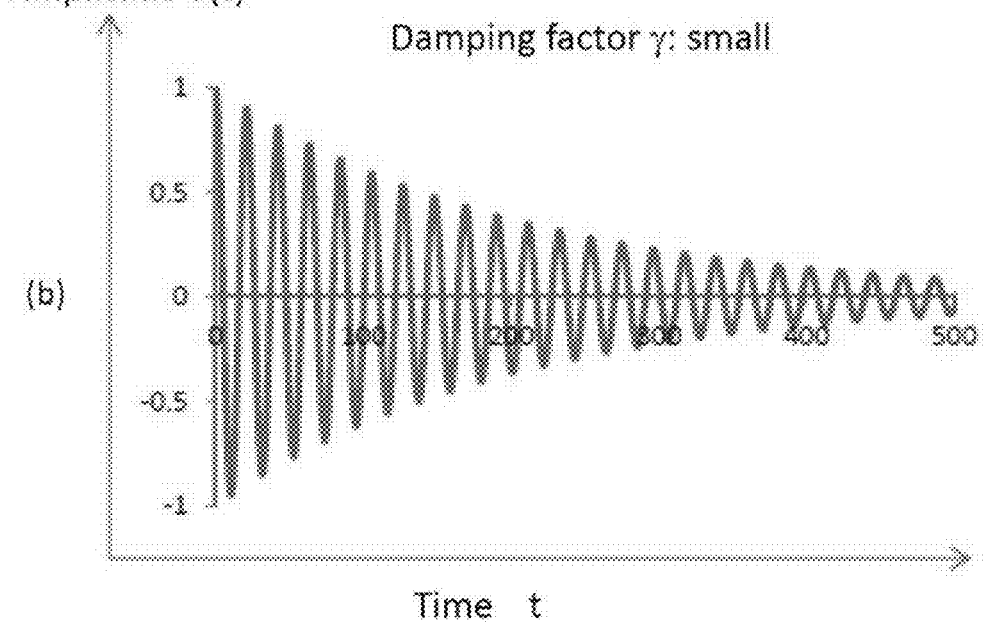
(b)

METHOD OF MEASURING THE ELASTICITY OF CRYSTALLINE LENS, A METHOD OF DETERMINING WHETHER CRYSTALLINE LENS IS PRESBYOPIC, AN APPARATUS FOR MEASURING THE ELASTICITY OF CRYSTALLINE LENS AND AN APPARATUS FOR DETERMINING WHETHER CRYSTALLINE LENS IS PRESBYOPIC

CROSS-REFERENCES TO RELATED APPLICATION

This application claims priority from Japanese Patent Application Ser. No. 2013-147897 filed Jul. 16, 2013, the contents of which are incorporated herein by reference in its entirety.

TECHNICAL FIELD

The present invention relates to a method of measuring the elasticity of crystalline lens for measuring stiffness of crystalline lens in a non-contact manner, a method of determining whether crystalline lens is presbyopic, an apparatus for measuring the elasticity of crystalline lens, and an apparatus for determining whether crystalline lens is presbyopic.

BACKGROUND

About half of a total population in Japan, eyes become presbyopia at 40 years old or higher, and most of eye disorders are associated with advancing age.

Under such circumstances, presbyopia is diagnosed by subjective inspection, and quantitative evaluation has not been conducted. Further, since it is difficult to grasp specific progress of presbyopia, presbyopia has not appropriately been medical treated.

For these reasons, quantitative evaluation of presbyopia is desired.

A cause of presbyopia is stiffening denaturation of protein in crystalline lens and following reduction of accommodation capability caused by the stiffened crystalline lens by advancing age.

Therefore, if it is possible to measure elasticity of a crystalline lens, quantitative diagnosis becomes possible.

As methods for measuring characteristics of eyes, research on methods using Raman scattering or stimulated Brillouin scattering is conducted.

According to the method using Raman scattering, stiffness of a crystalline lens and a state of progress of cataract are obtained from an amount of moisture in a crystalline lens.

According to the method using stimulated Brillouin scattering, an elasticity state of a corneae and a crystalline lens by a confocal optical system are obtained.

There is proposed an optical inspection apparatus for irradiating a front portion of an eye ball of a test subject with laser light, and measuring a state of an eye of the test subject from conditions of generated scattering light (Japanese Patent Application Laid-open No. S58-206718 and Japanese Patent Application Laid-open No. H6-217939).

Japanese Patent Application Laid-open No. S58-206718 proposes an eye ball opacity diagnostic apparatus for collecting emitted laser light at one point in an eye ball, receiving generated laser scattering light by a photoelectric conversion element to obtain a time correlation function, and calculating a diameter of protein.

Japanese Patent Application Laid-open No. H6-217939 proposes an ophthalmology measuring apparatus for irradiating an anterior segment of an eye ball with laser light, receiving scattering light from protein molecule or cell existing in aqueous humor in anterior chamber, receiving scattering light from corneae, and quantitatively obtaining protein concentration or cell density in aqueous humor in anterior chamber, and a degree of corneal opacity.

SUMMARY

The method using Raman scattering has a problem that basic research concerning a correlation between an amount of moisture and stiffness is required, and it is necessary to measure weak light and thus, the apparatus becomes complicated.

According to the method using Brillouin scattering, since elasticity is determined from extremely microscopic information by phonon, and this method does not measure the elasticity as a crystalline lens.

Japanese Patent Application Laid-open No. S58-206718 and Japanese Patent Application Laid-open No. H6-217939 are for measuring protein at a molecule level, and do not measure elasticity as a crystalline lens.

It is an object of the present invention to provide a method of measuring the elasticity of crystalline lens capable of instantaneously and quantitatively grasping an elasticity state of crystalline lens in a non-contact manner, and to provide a method of determining whether crystalline lens is presbyopic capable of quantitatively determining presbyopia.

The present invention provides a method of measuring the elasticity of crystalline lens for measuring stiffness of the crystalline lens, wherein the crystalline lens is irradiated with pulse laser light to generate photoelastic waves from the crystalline lens, and the photoelastic waves from the crystalline lens are measured.

In the method of measuring the elasticity of crystalline lens described above, the crystalline lens is irradiated with interference laser light to generate interference fringe by the photoelastic waves, and elastic modulus of the crystalline lens is calculated based on variation in the interference fringe.

Further, in the method of measuring the elasticity of crystalline lens described above, a wavelength of the pulse laser light is set such that light transmission in the crystalline lens becomes 20% or lower.

Further, in the method of measuring the elasticity of crystalline lens described above, a wavelength of the pulse laser light is set in a range of 1,400 nm to 2,600 nm.

Further, it is possible that elastic modulus of the crystalline lens is calculated by the method of measuring the elasticity of crystalline lens, and presbyopia caused by advancing age of the crystalline lens is determined from the calculated elastic modulus.

The present invention provides an apparatus for measuring the elasticity of crystalline lens for measuring stiffness of the crystalline lens, including a pumping laser for irradiating the crystalline lens with pulse laser light, an interference laser for irradiating the crystalline lens with interference laser light, a detector for measuring photoelastic waves from the crystalline lens, a calculating unit for calculating elastic modulus of the crystalline lens, and a display unit for displaying the elastic modulus calculated by the calculating unit.

The present invention provides an apparatus for determining whether crystalline lens is presbyopic for determining presbyopia caused by advancing age of the crystalline lens, including a pumping laser for irradiating the crystalline lens with pulse laser light, an interference laser for irradiating the crystalline lens with interference laser light, a detector for measuring photoelastic waves from the crystalline lens, a calculating unit for calculating elastic modulus of the crystalline lens, a presbyopia determining unit for determining the presbyopia caused by advancing age of the crystalline lens from the elastic modulus calculated by the calculating unit, and a display unit for displaying the elastic modulus calculated by the calculating unit and determination of presbyopia made by the presbyopia determining unit.

According to the present invention, it is possible to instantaneously and quantitatively grasp an elasticity state of crystalline lens in a non-contact manner by utilizing photoelastic waves generated in the crystalline lens.

BRIEF DESCRIPTION OF THE DRAWING

Other features and advantages of the method of measuring the elasticity of crystalline lens, the method of determining whether crystalline lens is presbyopic, the apparatus for measuring the elasticity of crystalline lens, and the apparatus for determining whether crystalline lens is presbyopic will be apparent from the ensuing description, taken in conjunction with the accompanying drawings, in which:

FIG. 3 are graphs showing damped vibration;

DESCRIPTION

Figure 1:
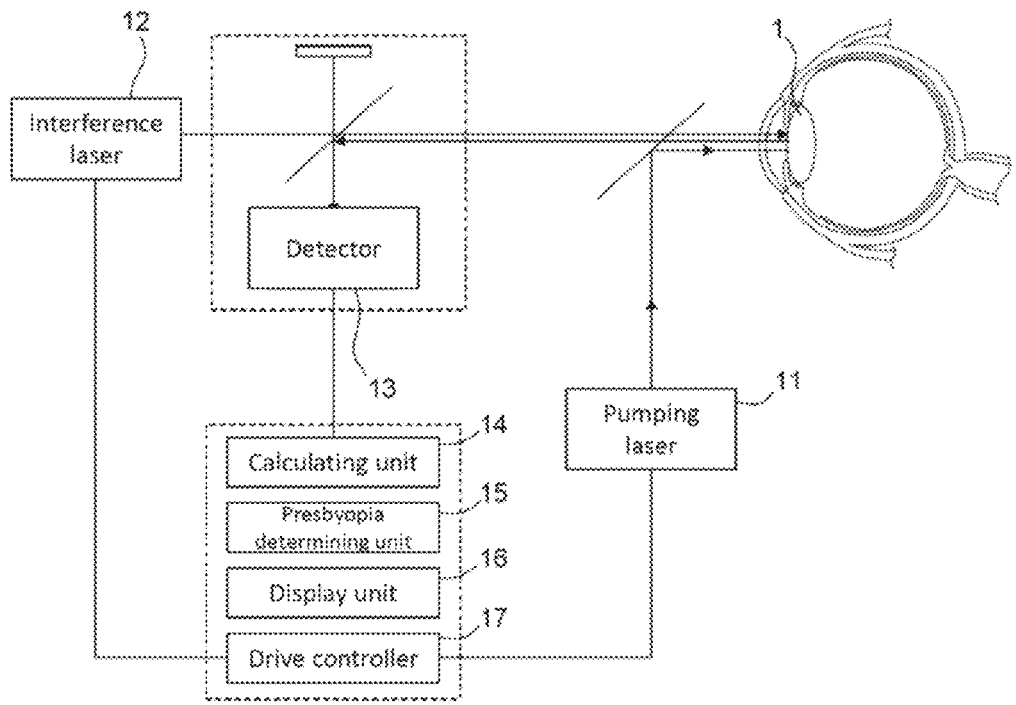
FIG. 1 is a block diagram for realizing a method of measuring the elasticity of crystalline lens according to an embodiment of the present invention.

A first aspect of the present invention provides a method of measuring the elasticity of crystalline lens, wherein the crystalline lens is irradiated with pulse laser light to generate photoelastic waves from the crystalline lens, and the photoelastic waves from the crystalline lens are measured. According to this aspect, by utilizing the photoelastic waves generated in the crystalline lens, it is possible to instantaneously and quantitatively grasp an elasticity state of the crystalline lens in a non-contact manner.

According to a second aspect of the invention, in the method of measuring the elasticity of crystalline lens of the first aspect, the crystalline lens is irradiated with interference laser light to generate interference fringe by the photoelastic waves, and elastic modulus of the crystalline lens is calculated based on variation in the interference fringe. According to this aspect, it is possible to carry out the measurement by weak pulse laser light.

According to a third aspect of the invention, in the method of measuring the elasticity of crystalline lens of the first or second aspect, a wavelength of the pulse laser light is set such that light transmission in the crystalline lens becomes 20% or lower. According to this aspect, it is possible to generate photoelastic waves by weak pulse laser light.

According to a fourth aspect of the invention, in the method of measuring the elasticity of crystalline lens of any one of the first to third aspects, a wavelength of the pulse laser light is set in a range of 1,400 nm to 2,600 nm. According to this aspect, it is possible to generate photoelastic waves without damaging the crystalline lens.

A fifth aspect of the invention provides a method of determining whether crystalline lens is presbyopic, wherein elastic modulus of the crystalline lens is calculated by the method of measuring the elasticity of crystalline lens according to any one of the first to fourth aspects, and presbyopia caused by advancing age of the crystalline lens is determined from the calculated elastic modulus. According to this aspect, it is possible to quantitatively measure presbyopia.

A sixth aspect of the invention provides an apparatus for measuring the elasticity of crystalline lens for measuring stiffness of the crystalline lens, including a pumping laser for irradiating the crystalline lens with pulse laser light, an interference laser for irradiating the crystalline lens with interference laser light, a detector for measuring photoelastic waves from the crystalline lens, a calculating unit for calculating elastic modulus of the crystalline lens, and a display unit for displaying the elastic modulus calculated by the calculating unit. According to this aspect, by utilizing photoelastic waves generated in the crystalline lens, it is possible to instantaneously and quantitatively grasp the elasticity state of the crystalline lens in a non-contact manner.

A seventh aspect of the invention provides an apparatus for determining whether crystalline lens is presbyopic for determining presbyopia caused by advancing age of the crystalline lens, including a pumping laser for irradiating the crystalline lens with pulse laser light, an interference laser for irradiating the crystalline lens with interference laser light, a detector for measuring photoelastic waves from the crystalline lens, a calculating unit for calculating elastic modulus of the crystalline lens, a presbyopia determining unit for determining the presbyopia caused by advancing age of the crystalline lens from the elastic modulus calculated by the calculating unit, and a display unit for displaying the elastic modulus calculated by the calculating unit and determination of presbyopia made by the presbyopia determining unit. According to this aspect, it is possible to quantitatively determine presbyopia.

Embodiments

FIG. 1 is a block diagram for realizing a method of measuring the elasticity of crystalline lens according to an embodiment of the present invention.

An apparatus for measuring the elasticity of crystalline lens according to the embodiment of the invention includes a pumping laser 11 for irradiating a crystalline lens 1 with pulse laser light, an interference laser 12 for irradiating the crystalline lens 1 with interference laser light, a detector 13 for measuring photoelastic waves from the crystalline lens 1, a calculating unit 14 for calculating elastic modulus of the crystalline lens 1, a presbyopia determining unit 15 for determining presbyopia caused by advancing age of the crystalline lens 1 from the elastic modulus calculated by the calculating unit 14, and a display unit 16 for displaying the elastic modulus calculated by the calculating unit 14 and determination of presbyopia made by the presbyopia determining unit 15.

The pumping laser 11 and the interference laser 12 emit light by a drive controller 17.

The method of measuring the elasticity of crystalline lens using the apparatus for measuring the elasticity of crystalline lens according to the present invention will be described.

The pumping laser 11 irradiates the crystalline lens 1 with pulse laser light to generate photoelastic waves from the crystalline lens 1.

The interference laser 12 irradiates crystalline lens 1 with interference laser light to generate interference fringe by the photoelastic waves.

The detector 13 detects the photoelastic waves from the crystalline lens 1 as variation in interference fringe.

The calculating unit 14 calculates the elastic modulus of the crystalline lens 1 from the variation in interference fringe detected by the detector 13.

Figure 2:
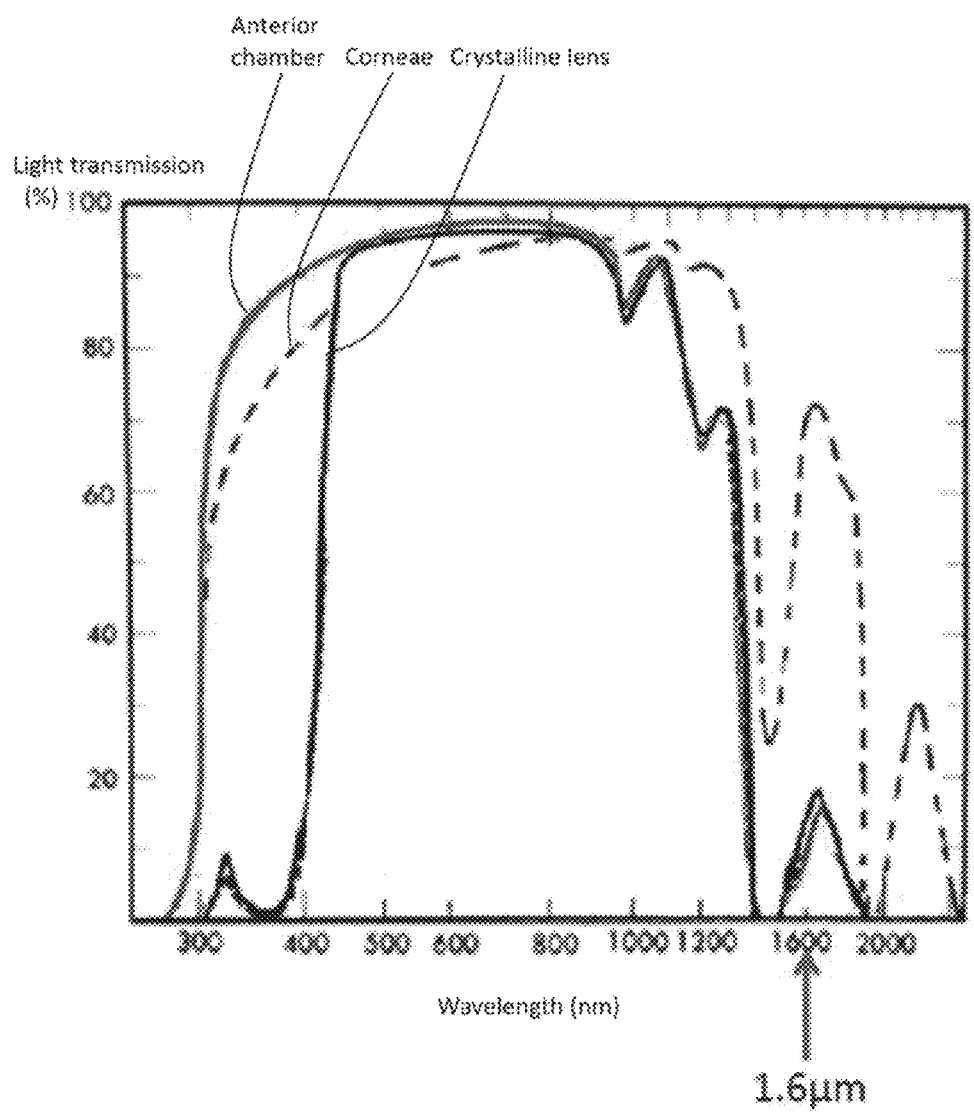
FIG. 2 is a diagram showing characteristics of light transmission in various portions of an eye ball.

FIG. 2 is a diagram showing characteristics of light transmission in various portions of an eye ball.

In FIG. 2, a horizontal axis shows a wavelength and a vertical axis shows light transmission, and FIG. 2 shows light transmission in a crystalline lens, an anterior chamber and a corneae.

Light having high light transmission in a cornea and an anterior chamber, and having low light transmission in the crystalline lens is suitable as the pulse laser light, and a wavelength having light transmission in a crystalline lens of 20% or lower, i.e., a wavelength in a range of 300 nm to 400 nm, or 1,400 nm to 2,600 nm is preferable.

Since there is a possibility that a wavelength of 300 nm to 400 nm damages DNA, a wavelength in a range of 1,400 nm to 2,600 nm is suitable for pulse laser light, and a wavelength of about 1,600 nm is most suitable.

FIG. 3 are graphs showing damped vibration, wherein FIG. 3 (a) shows a case where a damping factor γ is large and FIG. 3 (b) shows a case where the damping factor γ is small. The harder a subject to be measured is, the smaller a damping factor γ becomes.

The damped vibration is expressed by the following equation.

$$u(t) = A e^{-\gamma t} \cos(\sqrt{\omega_o^2 - \gamma^2}\, t + B)$$

Here, u (t) is amplitude after time t, A is amplitude when t=0, γ is a damping factor (viscosity damping coefficient), $\omega_o$ is natural angular frequency, and t is time.

The elastic modulus of the crystalline lens 1 is obtained by calculating the damping factor (viscosity damping coefficient) γ.

Figure 4:
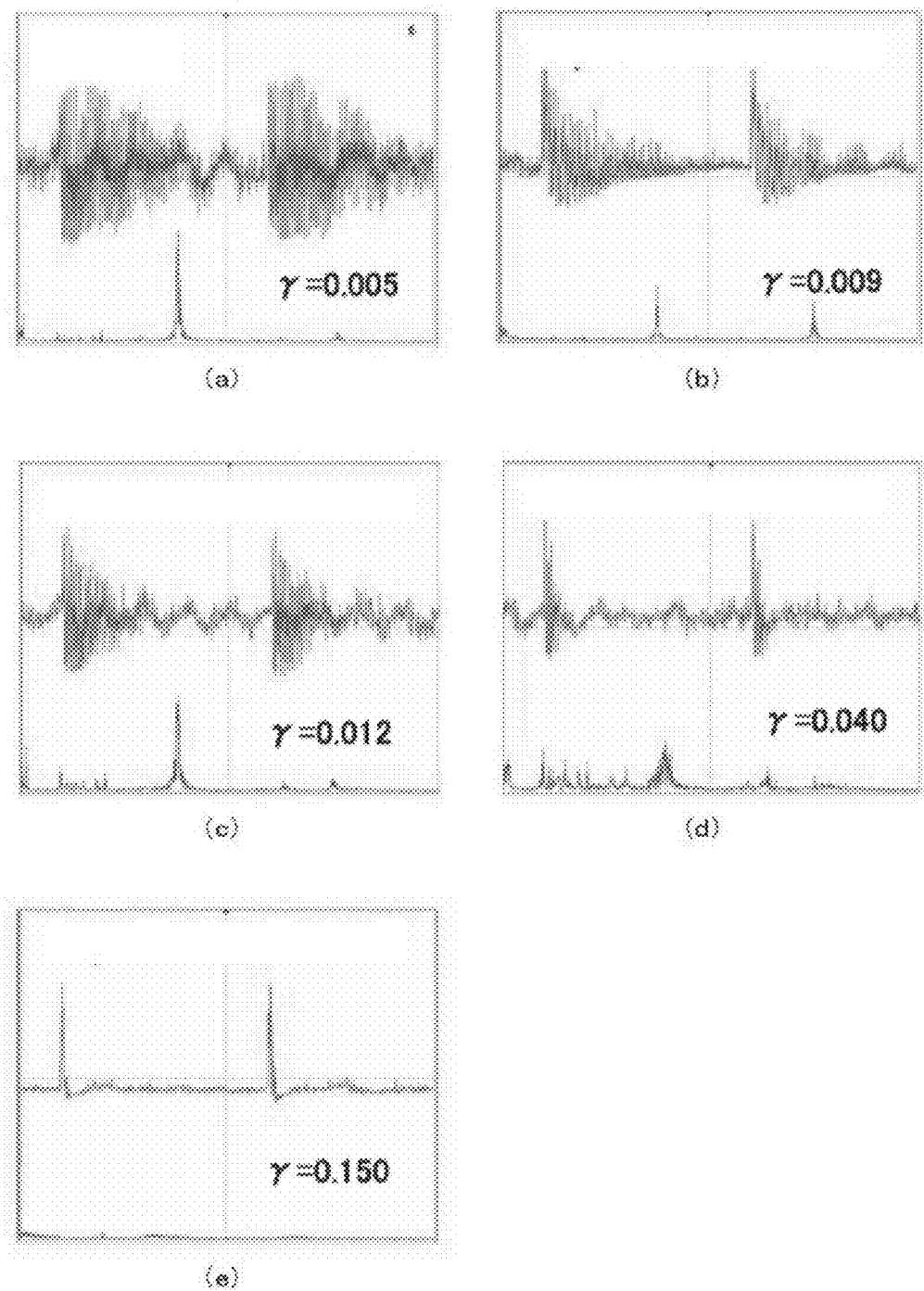
FIG. 4 show data measured by using a cover glass as a measurement sample and by changing hardness (damping factor) by pasting a tape of a different area on the cover glass.

FIG. 4 show data measured by using a cover glass as a measurement sample and by changing hardness (damping factor γ) by pasting a tape of a different area on the cover glass.

Pulse laser light having a wavelength of 355 nm was used.

FIG. 4 (a) shows damped vibration of a cover glass in a state where a tape is not pasted, FIG. 4 (b) shows damped vibration of a cover glass in a state where a tape of a vertical length 7.5 mm×a lateral length 7.5 mm is pasted, FIG. 4 (c) shows damped vibration of a cover glass in a state where a tape of a vertical length 15 mm×a lateral length 7.5 mm is pasted, FIG. 4 (d) shows damped vibration of a cover glass in a state where a tape of a vertical length 15 mm×a lateral length 15 mm is pasted, and FIG. 4 (e) shows damped vibration of a cover glass in a state where a tape of a vertical length 30 mm×a lateral length 15 mm is pasted, In FIG. 4 (a), the damping factor γ of the cover glass was 0.005. In FIG. 4 (b), the damping factor γ of the cover glass was 0.009. In FIG. 4 (c), the damping factor γ of the cover glass was 0.012. In FIG. 4 (d), the damping factor γ of the cover glass was 0.040. In FIG. 4 (e), the damping factor γ of the cover glass was 0.150.

Figure 5:
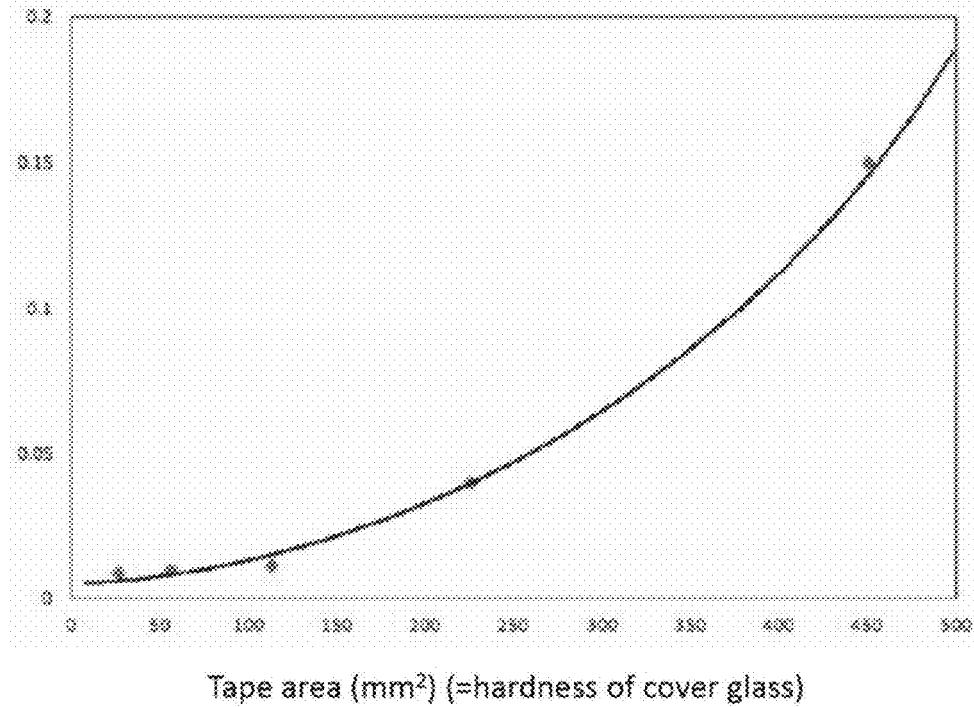
FIG. 5 shows a correlation between hardness of the cover glass and a damping factor based on the data shown in FIG. 4.

FIG. 5 shows a correlation between hardness of the cover glass and a damping factor based on the data shown in FIG. 4.

As shown in FIG. 5, it can be found that there is a correlation between hardness of the cover glass and a damping factor γ.

Therefore, if the correlation between the crystalline lens 1 and a damping factor γ is previously obtained, it is possible to quantitatively measure the elasticity of the crystalline lens 1, i.e., stiffening of the crystalline lens 1 caused by advancing age by calculating the damping factor γ of the crystalline lens 1.

Figure 6:
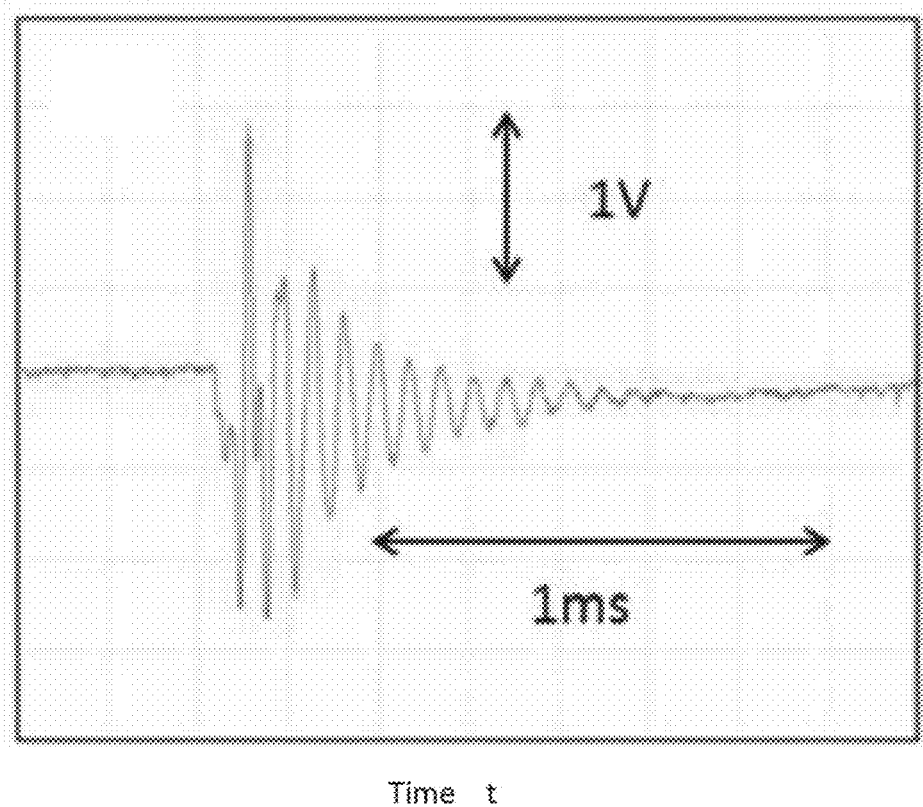
FIG. 6 is a graph showing an experiment result using a rat.

FIG. 6 is a graph showing an experiment result using a rat.

A crystalline lens 1 of a living rat was irradiated with pulse laser light having a wavelength of 355 nm, and an optoacoustic signal was measured. In this experiment, sound waves were detected using a microphone as the detector.

Photoelastic waves generated in the crystalline lens 1 can also be detected as sound waves as in this experiment.

As shown in FIG. 6, it is possible to optically non-invasively measure elasticity of the crystalline lens 1.

As described above, according to the embodiment, it is possible to instantaneously and quantitatively grasp an elasticity state of a crystalline lens 1 in a non-contact manner by utilizing the photoelastic waves generated by the crystalline lens 1.

According to the embodiment, the crystalline lens 1 is irradiated with interference laser light to generate interference fringe by the photoelastic waves, elastic modulus of the crystalline lens 1 is calculated based on variation in the interference fringe, and it is possible to conduct the measurement by weak pulse laser light.

By setting a wavelength of pulse laser light such that light transmission in a crystalline lens 1 becomes 20% or lower, photoelastic waves can be generated by weak pulse laser light.

Especially, if a wavelength of the pulse laser light is in a range of 1,400 nm to 2,600 nm, it is possible to generate photoelastic waves without damaging the crystalline lens 1.

If elastic modulus of the crystalline lens 1 is calculated by the method of measuring the elasticity of crystalline lens in this embodiment and presbyopia caused by advancing age of the crystalline lens 1 is determined based on the calculated elastic modulus, it is possible to quantitatively determine the presbyopia.

The present invention can be utilized at ophthalmology as diagnosis of presbyopia and inspection before cataract surgery.

The preceding description has been presented only to illustrate and describe exemplary embodiments of the present method of measuring the elasticity of crystalline lens, the method of determining whether crystalline lens is presbyopic, the apparatus for measuring the elasticity of crystalline lens, and the apparatus for determining whether crystalline lens is presbyopic. It is not intended to be exhaustive or to limit the invention to any precise form disclosed. It will be understood by those skilled in the art that various changes may be made and equivalents may be substituted for elements thereof without departing from the scope of the invention. In addition, many modifications may be made to adapt a particular situation or material to the teachings of the invention without departing from the essential scope. Therefore, it is intended that the invention not be limited to the particular embodiment disclosed as the best mode contemplated for carrying out this invention, but that the invention will include all embodiments falling within the scope of the claims. The invention may be practiced otherwise than is specifically explained and illustrated without departing from its spirit or scope.

What is claimed is:

1. A method of measuring the elasticity of crystalline lens for measuring stiffness of the crystalline lens,
wherein the crystalline lens is irradiated with pulse laser light to generate photoelastic waves from the crystalline lens, and the photoelastic waves from the crystalline lens are measured whereby a damping factor of the crystalline lens is calculated, the crystalline lens is irradiated with interference laser light to generate interference fringe by the photoelastic waves, and elastic modulus of the crystalline lens is calculated based on variation in the interference fringe, and a wavelength of the pulse laser light is set such that light transmission in the crystalline lens becomes 20% or lower.

2. The method according to claim 1, wherein a wavelength of the pulse laser light is set in a range of 1,400 nm to 2,600 nm.

3. A method of determining whether crystalline lens is presbyopic, wherein elastic modulus of the crystalline lens is calculated by the method according to claim 1, and presbyopia caused by advancing age of the crystalline lens is determined from the calculated elastic modulus.

4. An apparatus for measuring the elasticity of crystalline lens for measuring stiffness of the crystalline lens, comprising:
   a pumping laser for irradiating the crystalline lens with pulse laser light,
   an interference laser for irradiating the crystalline lens with interference laser light,
   a detector for measuring photoelastic waves from the crystalline lens,
   a calculating unit for calculating elastic modulus of the crystalline lens, and
   a display unit for displaying the elastic modulus calculated by the calculating unit,
   wherein the photoelastic waves from the crystalline lens are measured whereby a damping factor of the crystalline lens is calculated.

5. An apparatus for determining whether crystalline lens is presbyopic for determining presbyopia caused by advancing age of the crystalline lens, comprising
   a pumping laser for irradiating the crystalline lens with pulse laser light,
   an interference laser for irradiating the crystalline lens with interference laser light,
   a detector for measuring photoelastic waves from the crystalline lens,
   a calculating unit for calculating elastic modulus of the crystalline lens,
   a presbyopia determining unit for determining the presbyopia caused by advancing age of the crystalline lens from the elastic modulus calculated by the calculating unit, and
   a display unit for displaying the elastic modulus calculated by the calculating unit and determination of presbyopia made by the presbyopia determining unit.

* * * * *